(12) United States Patent
Defreitas et al.

(10) Patent No.: US 12,064,291 B2
(45) Date of Patent: *Aug. 20, 2024

(54) TOMOSYNTHESIS-GUIDED BIOPSY IN PRONE

(71) Applicant: Hologic, Inc., Marlborough, MA (US)

(72) Inventors: Kenneth F. Defreitas, Patterson, NY (US); Ian Shaw, Yorktown Heights, NY (US); John Laviola, Orange, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,207

(22) Filed: Jan. 27, 2023

(65) Prior Publication Data

US 2023/0240785 A1 Aug. 3, 2023

Related U.S. Application Data

(63) Continuation of application No. 16/576,510, filed on Sep. 19, 2019, now Pat. No. 11,589,944, which is a
(Continued)

(51) Int. Cl.
*A61B 6/02* (2006.01)
*A61B 6/00* (2024.01)
(Continued)

(52) U.S. Cl.
CPC .............. *A61B 90/11* (2016.02); *A61B 6/025* (2013.01); *A61B 6/0414* (2013.01);
(Continued)

(58) Field of Classification Search
CPC ....... A61B 6/025; A61B 6/0414; A61B 6/502; A61B 90/11
See application file for complete search history.

(56) References Cited

U.S. PATENT DOCUMENTS 3,502,878 A 3/1970 Stewart
3,863,073 A 1/1975 Wagner
(Continued)

FOREIGN PATENT DOCUMENTS

AU 2014339982 4/2015
CN 1802121 A 7/2006
(Continued)

OTHER PUBLICATIONS

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.
(Continued)

*Primary Examiner* — Colin T. Sakamoto
(74) *Attorney, Agent, or Firm* — Merchant & Gould P.C.

(57) ABSTRACT

A station for tomotactic-guided biopsy in prone includes a table with an aperture, and a tomosynthesis imaging system. A biopsy gun can be mounted on a stage arm assembly disposed below the table. The imaging system and stage arm assembly can be independently rotated and linearly repositioned in one or more dimensions, thereby allowing the tomotactic scan axis to be located relative to a breast being imaged.

20 Claims, 8 Drawing Sheets

Related U.S. Application Data continuation of application No. 16/127,564, filed on Sep. 11, 2018, now Pat. No. 10,456,213, which is a continuation of application No. 14/777,199, filed as application No. PCT/US2014/026164 on Mar. 13, 2014, now Pat. No. 10,092,358.

(60) Provisional application No. 61/787,825, filed on Mar. 15, 2013.

(51) Int. Cl.
| | | |
|---|---|---|
| A61B 6/04 | (2006.01) | |
| A61B 6/50 | (2024.01) | |
| A61B 90/11 | (2016.01) | |
| A61B 6/12 | (2006.01) | |
| A61B 10/02 | (2006.01) | |
| A61B 10/04 | (2006.01) | |

(52) U.S. Cl.
CPC ............ *A61B 6/0435* (2013.01); *A61B 6/502* (2013.01); *A61B 6/12* (2013.01); *A61B 6/4452* (2013.01); *A61B 10/0233* (2013.01); *A61B 2010/045* (2013.01)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A | 7/2000 | Cundari et al. |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |

(56) References Cited

U.S. PATENT DOCUMENTS

| | | |
|---|---|---|
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 | 7/2009 | Wang et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 | 9/2018 | Robinson et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 | 4/2019 | Reicher et al. |
| 10,282,840 B2 | 5/2019 | Moehrle et al. |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 11,589,944 B2 | 2/2023 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 | 10/2003 | Suzuki et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |

(56) References Cited

U.S. PATENT DOCUMENTS

| | | |
|---|---|---|
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Lomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1 | 7/2006 | Ma et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1* | 2/2008 | Hassanpourgol .... A61B 6/0435 606/130 |
| 2008/0045833 A1 | 2/2008 | DeFreitas et al. |
| 2008/0101537 A1* | 5/2008 | Sendai ................... A61B 6/025 378/23 |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas et al. |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1 | 3/2009 | Dachille et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1* | 3/2009 | Shores .................. A61B 6/487 378/37 |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1* | 7/2009 | Ning .................... A61B 6/0435 378/37 |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1* | 3/2010 | Kojima ................. A61B 6/502 378/11 |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0171764 A1 | 7/2010 | Feng et al. |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1 | 9/2010 | Chen et al. |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0123073 A1 | 5/2011 | Gustafson |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1 | 6/2011 | Bernard et al. |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0131488 A1 | 5/2012 | Karlsson et al. |

(56) References Cited

U.S. PATENT DOCUMENTS

| | | |
|---|---|---|
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0150034 A1 | 6/2012 | DeFreitas et al. |
| 2012/0189092 A1 | 7/2012 | Jerebko |
| 2012/0194425 A1 | 8/2012 | Buelow |
| 2012/0238870 A1 | 9/2012 | Smith et al. |
| 2012/0277625 A1* | 11/2012 | Nakayama ........... A61B 6/0414 250/393 |
| 2012/0293511 A1 | 11/2012 | Mertelmeier |
| 2013/0016255 A1 | 1/2013 | Bhatt |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1* | 10/2013 | Packard ................ A61B 6/502 378/37 |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0082542 A1 | 3/2014 | Zhang et al. |
| 2014/0200433 A1 | 7/2014 | Choi |
| 2014/0219534 A1 | 8/2014 | Wiemker et al. |
| 2014/0219548 A1 | 8/2014 | Wels |
| 2014/0276061 A1 | 9/2014 | Lee et al. |
| 2014/0327702 A1 | 11/2014 | Kreeger et al. |
| 2014/0328517 A1 | 11/2014 | Gluncic |
| 2015/0052471 A1 | 2/2015 | Chen |
| 2015/0061582 A1 | 4/2015 | Smith |
| 2015/0238148 A1 | 8/2015 | Georgescu |
| 2015/0258271 A1 | 9/2015 | Love |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0210774 A1 | 7/2016 | Wiskin et al. |
| 2016/0228034 A1 | 8/2016 | Gluncic |
| 2016/0235380 A1 | 8/2016 | Smith |
| 2016/0350933 A1 | 12/2016 | Schieke |
| 2016/0364526 A1 | 12/2016 | Reicher et al. |
| 2016/0367210 A1 | 12/2016 | Gkanatsios |
| 2017/0071562 A1 | 3/2017 | Suzuki |
| 2017/0132792 A1 | 5/2017 | Jerebko et al. |
| 2017/0262737 A1 | 9/2017 | Rabinovich |
| 2018/0008220 A1 | 1/2018 | Boone et al. |
| 2018/0008236 A1 | 1/2018 | Venkataraman et al. |
| 2018/0047211 A1 | 2/2018 | Chen et al. |
| 2018/0109698 A1 | 4/2018 | Ramsay et al. |
| 2018/0132722 A1 | 5/2018 | Eggers et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0000318 A1 | 1/2019 | Caluser |
| 2019/0015173 A1 | 1/2019 | DeFreitas |
| 2019/0037173 A1 | 1/2019 | Lee et al. |
| 2019/0043456 A1 | 2/2019 | Kreeger |
| 2019/0057778 A1 | 2/2019 | Porter et al. |
| 2019/0287241 A1 | 9/2019 | Hill et al. |
| 2019/0290221 A1 | 9/2019 | Smith |
| 2019/0325573 A1 | 10/2019 | Bernard et al. |
| 2020/0046303 A1 | 2/2020 | DeFreitas |
| 2020/0054300 A1 | 2/2020 | Kreeger et al. |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2022/0005277 A1 | 1/2022 | Chen |
| 2022/0013089 A1 | 1/2022 | Kreeger |
| 2022/0036545 A1 | 2/2022 | St. Pierre |
| 2022/0192615 A1 | 6/2022 | Chui |
| 2022/0254023 A1 | 8/2022 | McKinney et al. |
| 2022/0386969 A1 | 12/2022 | Smith |
| 2023/0008465 A1 | 1/2023 | Smith |
| 2023/0033601 A1 | 2/2023 | Chui |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0098305 A1 | 3/2023 | St. Pierre |
| 2023/0103969 A1 | 4/2023 | St. Pierre |
| 2023/0124481 A1 | 4/2023 | St. Pierre |
| 2023/0125385 A1 | 4/2023 | Solis |
| 2023/0225821 A1 | 7/2023 | DeFreitas |

FOREIGN PATENT DOCUMENTS

| | | |
|---|---|---|
| CN | 1846622 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 | 7/2015 |
| EP | 3060132 | 4/2019 |
| JP | H09-35043 | 2/1997 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008-253401 | 10/2008 |
| JP | 2009-034503 | 2/2009 |
| JP | 2009-522005 | 6/2009 |

(56) References Cited

FOREIGN PATENT DOCUMENTS

| | | |
|---|---|---|
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Canadian Office Action in Application 2829349, mailed Oct. 15, 2018, 4 pages.

Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", Br J Radiol. Apr. 2010;83 (988):344-50.

Chan, Heang-Ping et al., "Computer-aided detection system for breast masses on digital tomosynthesis mammograms: Preliminary Experience", Radiology, Dec. 2005, 1075-1080.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Chinese 2nd Office Action in Application 201480058064.5, mailed Jul. 16, 2019, 5 pgs.

Conner, Peter, "Breast Response to Menopausal Hormone Therapy—Aspects on Proliferation, apoptosis and Mammographic Density", 2007 Annals of Medicine, 39;1, 28-41.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

Dromain, Clarisse, et al., "Evaluation of tumor angiogenesis of breast carcinoma using contrast-enhanced digital mammography", AJR: 187, Nov. 2006, 16 pages.

E. Shaw de Paredes et al., "Interventional Breast Procedure", published Sep./Oct. 1998 in Curr Probl Diagn Radiol, pp. 138-184.

(56) References Cited

OTHER PUBLICATIONS eFilm Mobile HD by Merge Healthcare, web site: http://itunes.apple.com/bw/app/efilm-mobile-hd/id405261243?mt=8, accessed on Nov. 3, 2011 (2 pages).
eFilm Solutions, eFilm Workstation (tm) 3.4, website: http://estore.merge.com/na/estore/content.aspx?productID=405, accessed on Nov. 3, 2011 (2 pages).
Elbakri, Idris A. et al., "Automatic exposure control for a slot scanning full field digital mammography system", Med. Phys. Sep. 2005; 32(9):2763-2770, Abstract only.
Ertas, M. et al., "2D versus 3D total variation minimization in digital breast tomosynthesis", 2015 IEEE International Conference on Imaging Systems and Techniques (IST), Macau, 2015, pp. 1-4.
European Acknowledgment of Receipt in Opposition Proceedings in relation to EP18153706.9, date stamped Feb. 18, 2021, 59 pages.
European Brief Communication & Response in Opposition Proceedings in relation to EP18153706.9, filed Oct. 12, 2021, 272 pages.
European Brief Communication in Application 18153706.9, mailed Feb. 24, 2021, 58 pages.
European Communication in Application 10707751.3, mailed Oct. 4, 2018, 5 pages.
European Communication in Application 10707751.3, mailed Aug. 7, 2019, 6 pages.
European Communication of a Notice of Opposition in Application 18153706.9, mailed Sep. 21, 2020, 35 pages.
European Extended Search Report dated Jul. 18, 2014 in EP App 12754521.8, 7 pages.
European Extended Search Report for European Patent Application No. 14770362.3 mailed Sep. 28, 2016, 8 pgs.
European Extended Search Report in Application 14855181.5, mailed May 15, 2017, 7 pages.
European extended Search Report in Application 18153706.9, mailed Jun. 1, 2018, 8 pages.
European Final Written Submissions in Opposition Proceedings in relation to EP18153706.9, date stamped Oct. 6, 2021, 144 pages.
European Mar. 23, 2009, European Search Report in connection with counterpart European patent Application No. 07750818.
European Statement of Grounds of Appeal and Auxiliary Requests filed in European Application 18153706.9 on Jun. 24, 2022, 164 pages.
European Summons to Attend Oral Proceedings in Application 18153706.9, mailed Apr. 26, 2021, 23 pages.
European Written Submissions and contact details as filed in Application 18153706.9, filed Oct. 6, 2021, 26 pages.
Feng, Steve Si Jia, et al., "Clinical digital breast tomosynthesis system: Dosimetric Characterization", Radiology, Apr. 2012, 263(1); pp. 35-42.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Freiherr, G., "Breast tomosynthesis trials show promise", Diagnostic Imaging—San Francisco 2005, V27; N4:42-48.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Ghiassi, M. et al., "A Dynamic Architecture for Artificial Networks", Neurocomputing, vol. 63, Aug. 20, 2004, pp. 397-413.
Giger et al. "Development of a smart workstation for use in mammography", in Proceedings of SPIE, vol. 1445 (1991), pp. 101103; 4 pages.
Giger et al., "An Intelligent Workstation for Computer-aided Diagnosis", in RadioGraphics, May 1993, 13:3 pp. 647-656; 10 pages.
Glick, Stephen J., "Breast CT", Annual Rev. Biomed. Eng., 2007, 9;501-26.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Ijaz, Umer Zeeshan, et al., "Mammography phantom studies using 3D electrical impedance tomography with numerical forward solver", Frontiers in the Convergence of Bioscience and Information Technologies 2007, 379-383.
Japanese Notice of Final Rejection in Application 2016-526115, mailed Jun. 24, 2019, 5 pages.
Jochelson, M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, Daniel B., "Breast Imaging", 3rd Edition, Lippincott Williams and Wilkins, published Nov. 2, 2006, pp. 960-967.
Kopans, et. al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin,JM, et al., Dual-energy contrast-enhanced digital subtraction mammography: feasibility. Radiology 2003; 229:261-268.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Lindfors, KK, et al., Dedicated breast CT: initial clinical experience. Radiology 2008; 246(3): 725-733.
Mahesh, Mahadevappa, "AAPM/RSNA Physics Tutorial for Residents—Digital Mammography: An Overview", Nov.-Dec. 2004, vol. 24, No. 6, 1747-1760.
Metheany, Kathrine G et al., "Characterizing anatomical variability in breast CT images", Oct. 2008, Med. Phys. 35 (10); 4685-4694.
Niklason, L., et al., Digital tomosynthesis in breast imaging. Radiology. Nov. 1997; 205(2):399-406.
Observations by Third Party, Remarks concerning European patent application No. 10707751.3 according to Article 115 EPC, dated Apr. 24, 2014, 8 pgs.
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
PCT Feb. 20, 2008, International Search Report and Written Opinion in connection with corresponding International patent application No. PCT/US2007/04006, 7 pgs.
PCT International Preliminary Report on Patentability in International Application PCT/US2014/061994, mailed Apr. 26, 2016, 5 pages.
PCT International Search Report and Written Opinion in Application PCT/US2010/025873, dated Aug. 2, 2010, 19 pgs.
PCT International Search Report in Application PCT/US2014/026164, mailed Jul. 28, 2014, 1 page.
PCT International Written Report for International Application PCT/US2014/026164, mailed Jul. 28, 2014, 2 pgs.

(56) References Cited

OTHER PUBLICATIONS

PCT Written Opinion in International Application PCT/US2014/061994, mailed Jan. 22, 2015, 4 pages.
PCT/US12/28334 International Search Report and Written Opinion, dated Jul. 5, 2012, 7 pages.
Pediconi, "Color-coded automated signal intensity-curve for detection and characterization of breast lesions: Preliminary evaluation of new software for MR-based breast imaging," International Congress Series 1281 (2005) 1081-1086.
Poplack, SP, et al., Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.
Sechopoulos, et al., "Glandular radiation dose in tomosynthesis of the breast using tungsten targets", Journal of Applied Clinical Medical Physics, vol. 8, No. 4, Fall 2008, 161-171.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Taghibakhsh, F. et al., "High dynamic range 2-TFT amplified pixel sensor architecture for digital mammography tomosynthesis", IET Circuits Devices Syst., 2007, 1(1), pp. 87-92.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis vols. with a computer-aided detection system trained on 2D mammograms", Med. Phys. 40(4), Apr. 2013, 41902-1-41902-11.

Varjonen, Mari, "Three-Dimensional Digital Breast Tomosynthesis in the Early Diagnosis and Detection of Breast Cancer", IWDM 2006, LNCS 4046, 152-159.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Wen, Junhai et al., "A study on truncated cone-beam sampling strategies for 3D mammography", 2004, IEEE, 3200-3204.
Williams, Mark B. et al., "Optimization of exposure parameters in full field digital mammography", Medical Physics 35, 2414 (May 20, 2008); doi: 10.1118/1.2912177, pp. 2414-2423.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Zhang, Yiheng et al., "A comparative study of limited-angle cone-beam reconstruction methods for breast tomosythesis", Med Phys., Oct. 2006, 33(10): 3781-3795.
Zhao, Bo, et al., "Imaging performance of an amorphous selenium digital mammography detector in a breast tomosynthesis system", May 2008, Med. Phys 35(5); 1978-1987.
Cho, N. et al., "Distinguishing Benign from Malignant Masses at Breast US: Combined US Elastography and Color Doppler US-Influence on Radiologist Accuracy", Radiology, 262(1): 80-90 (Jan. 2012).
Green, C. et al., "Deformable mapping using biochemical models to relate corresponding lesions in digital breast tomosynthesis and automated breast ultrasound images", Medical Image Analysis, 60: 1-18 (Nov. 2019).
Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.
Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).
Love, Susan M., et al. "Anatomy of the nipple and breast ducts revisited", Cancer, American Cancer Society, Philadelphia, PA, vol. 101, No. 9, Sep. 20, 2004, pp. 1947-1957.

\* cited by examiner

BIOPSY STATION 100

TOMOSYNTHESIS-GUIDED BIOPSY IN PRONE

CROSS-REFERENCE TO RELATED APPLICATIONS

This application is a continuation of U.S. patent application Ser. No. 16/576,510, now U.S. Pat. No. 11,589,944, filed Sep. 19, 2019, which is a continuation of U.S. patent application Ser. No. 16/127,564, now U.S. Pat. No. 10,456,213, filed Sep. 11, 2018, which is a continuation of U.S. patent application Ser. No. 14/477,199, now U.S. Pat. No. 10,092,358, filed Sep. 15, 2015, which is a National Stage of PCT International Patent Application No. PCT/US2014/026164, filed Mar. 13, 2014, which claims the benefit of U.S. Provisional Patent Application No. 61/787,825, filed Mar. 15, 2013 all of which are incorporated herein by reference in their entireties.

BACKGROUND

The subject matter of this disclosure is generally related to the medical field. Medical imaging technologies such as stereotactic x-ray, fluoroscopy, computer tomography, ultrasound, nuclear medicine and magnetic resonance imaging enable detection of small abnormalities in the body of a patient. The discovery of certain abnormalities may prompt performance of a biopsy procedure to obtain a tissue sample for lab analysis to help diagnose and treat patients suspected of having cancerous tumors, pre-malignant conditions or other diseases or disorders. The biopsy may be either an open surgical procedure or a percutaneous procedure. Percutaneous biopsy is often preferable to an open surgical biopsy in the case of small abnormalities located deep within the body because a percutaneous biopsy removes a relatively small amount of tissue. For example, a biopsy needle can be used to remove individual cells or clusters of cells in the case of fine needle aspiration (FNA), and a core or fragment of tissue in the case of a core biopsy.

A biopsy gun and guidance system may be used to move the biopsy needle with precision along a planned path in order to obtain a suitable sample of the abnormality. An example of a stereotactic guided lateral arm system is disclosed in U.S. Published Patent Application 2001/0087132 A1, Ser. No. 12/715,591, titled NEEDLE BREAST BIOPSY SYSTEM AND METHOD FOR USE, which is incorporated by reference. In order to perform a biopsy procedure the breast is placed in compression and Multiple x-ray images are used to localize the abnormality and perform final adjustments of the needle guidance system. One technological challenge in designing guided biopsy systems is that the biopsy needle may create undesirable artifacts in the images. For example, in a configuration where the biopsy needle is aligned with the path between the x-ray source and x-ray detector a portion of the needle may reside in the path and consequently be imaged. Another technological challenge is accommodation of relatively thin breasts. A "side entry" may be the only practical option for biopsy of a thin breast under compression. The lateral arm may be detached and reattached in order to set up for such a procedure. However, various manual calculations may be required in order to prepare for the procedure and the breast platform or x-ray detector may interfere with the path of the biopsy gun due to space limitations. These technological challenges may become even more complex if tomotactic guidance is used rather than stereotactic guidance. Tomotactic guidance is based on tomosynthesis imaging. As disclosed in U.S. Published Patent Application 2008/0045833 A1, Ser. No. 11/707,587, titled BREAST BIOPSY AND NEEDLE LOCALIZATION USING TOMOSYNTHESSIS SYSTEMS, which is incorporated by reference, exposures at angles where the biopsy gun would cause artifacts to appear in the image can be skipped. In general, however, a breast biopsy system that would help solve some or all of these challenges would be desirable.

SUMMARY

According to an aspect an apparatus includes: a table for supporting a patient in a prone position; a tomosynthesis imaging system disposed below the table for imaging a breast of the patient; and a stage arm assembly which positions a biopsy needle to obtain a tissue sample from the portion of the patient imaged by the tomosynthesis imaging system.

According to another aspect a method includes: positioning a patient on a table in a prone position; imaging a portion of the patient with a tomosynthesis imaging system disposed below the table; positioning a biopsy needle by configuring a stage arm assembly using information from the tomosynthesis imaging system; and obtaining a tissue sample from the portion of the patient imaged by the tomosynthesis imaging system.

Advantages include simple and flexible set up. The table may have an aperture through which the breast undergoing biopsy extends with the patient in a prone position. Non-limiting examples of known prone approaches for imaging and/or biopsy include PCT Publication No. WO 2012/112627, U.S. Patent Application Publication Nos. 2009/0080604 and 2009/171244, and U.S. Pat. Nos. 6,480,565, 6,987,331, and 7,697,660, each of which is incorporated by reference herein in their entireties. Moreover, the aperture may be disposed approximately midway along the length of the table so that the table may accommodate 180 degree repositioning of the patient. The stage arm assembly and imaging system may be independently rotatable for set up, e.g., each through a 180° range of arc, without being detached and reattached or using optional parts. Various linear adjustments may also be possible. Consequently, the breast of a patient in a prone position can be accessed through a range of 360 degrees in various planes via a combination of reversing the position of the patient and simple rotational and linear adjustments of the stage arm assembly and imaging system.

Another advantage is accommodation of relatively thin breasts. Due to the relative size and location of cutting features of the biopsy needle it may be necessary or desirable to perform a "side entry" biopsy procedure relative to the axis of compression. Certain aspects may allow use of a relatively small x-ray receptor that enables enhanced geometry of other features in order to reduce the possibility of interference with the biopsy gun. For example, the x-ray receptor and x-ray energy source may be mounted on a support structure such as a c-arm which maintains the source and receptor in alignment at a fixed distance during a scan or sweep such that both the detector and the receptor move arcuately, thereby allowing receptor size to be reduced. The detector may also be offset from a breast support platform by a distance on the order of several centimeters. Reduced receptor size and offset from the breast support platform allow reduction of the size of the surface supporting the breast. Reduction of the size of the supporting surface allows adjacent side-edge sections to be angled or curved away such that interference with the biopsy gun is avoided, thereby facilitating side entry biopsy of relatively thin breasts.

Another advantage is mitigation or elimination of image artifacts caused by the biopsy needle. The stage arm, and thus the gun mount and biopsy needle, may be oriented at a fixed inclination, e.g., 10°, relative to the plane in which the stage arm assembly is rotatable. Inclination of the stage arm allows a "zero degree" offset configuration in which the stage arm assembly is aligned with the imaging system. Optionally, the stage arm can be positioned on an axis offset from that of the imaging system. In particular, the inclined biopsy gun and needle reside above or below rather than in the field of view of the imaging system so the images are free of biopsy needle artifacts.

Unless specifically stated otherwise, the features described herein can be used in any combination, and the aspects can include any one or more of the embodiments. Moreover, other features and advantages will become apparent to those of ordinary skill in the art in view of the figures and detailed description.

DETAILED DESCRIPTION

Figure 1:
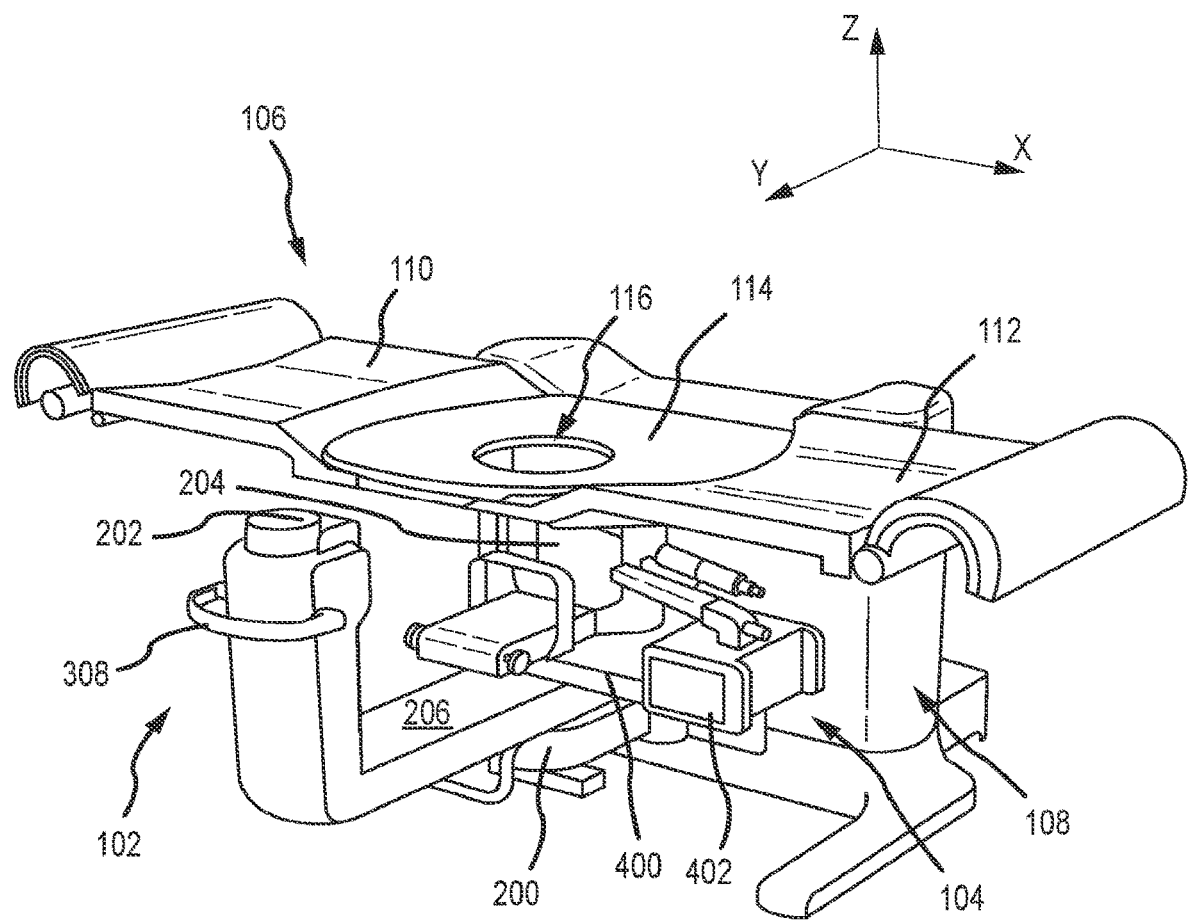
FIG. 1 is an isometric view of a tomotactic guided biopsy station.
Figure 2:
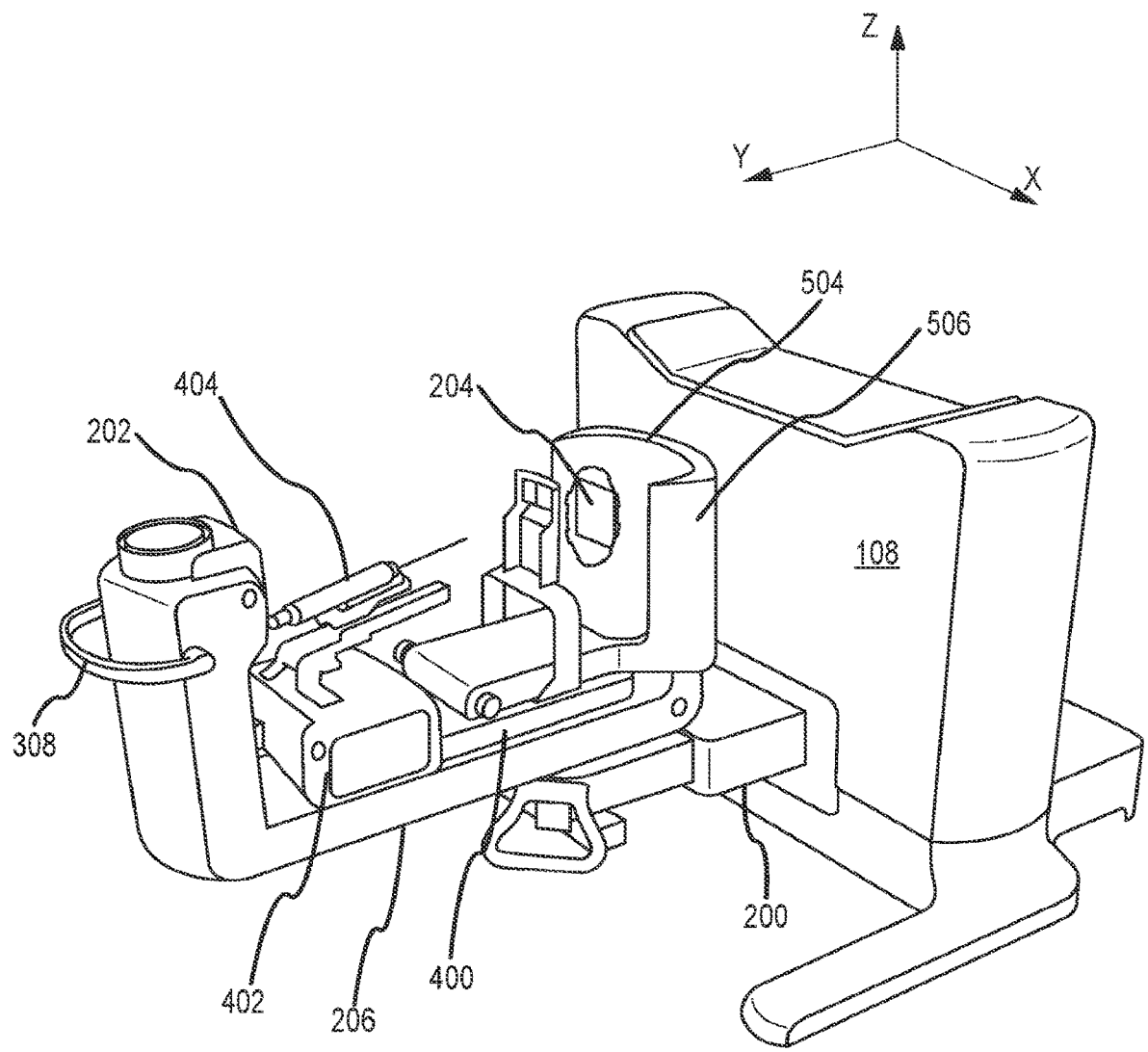
FIG. 2 illustrates the station of FIG. 1 in a zero degree offset configuration with the table top removed to better illustrate certain features such as the x-ray receptor which is shown via a cutaway of the breast platform.
Figure 3:
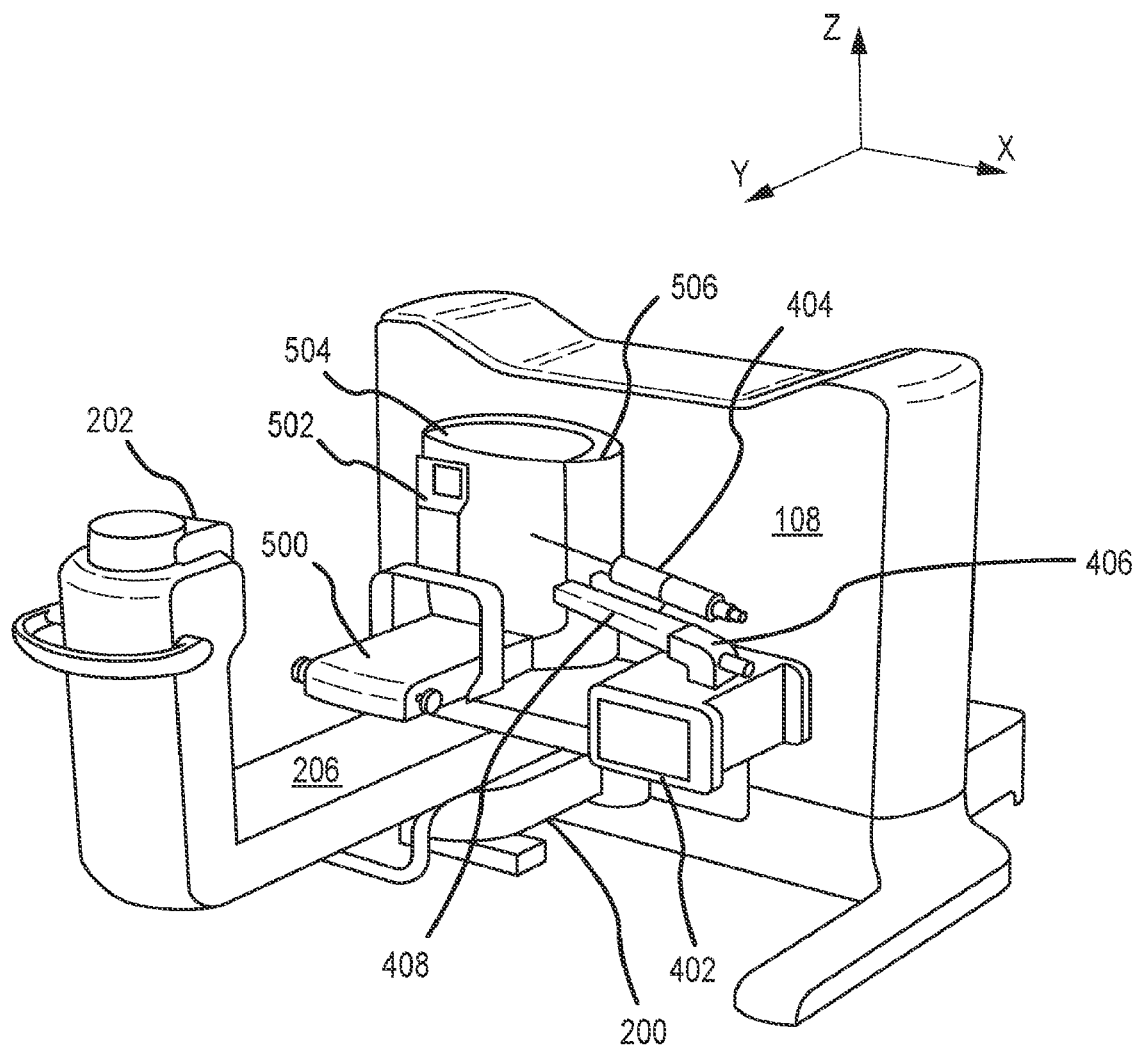
FIGS. 3-7 are various views of the station of FIG. 2 in a ninety degree offset configuration.
Figure 4:
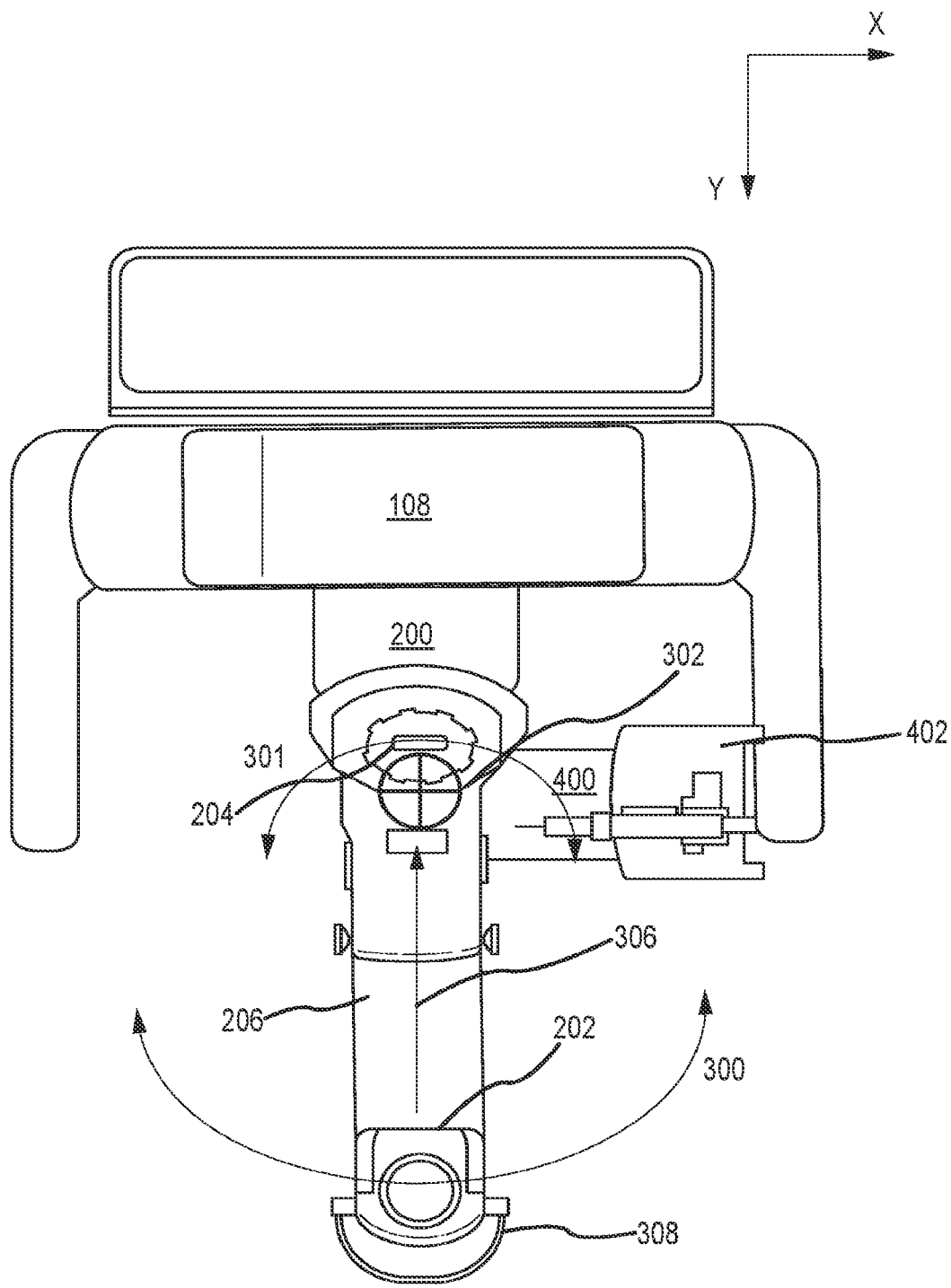
Figure 5:
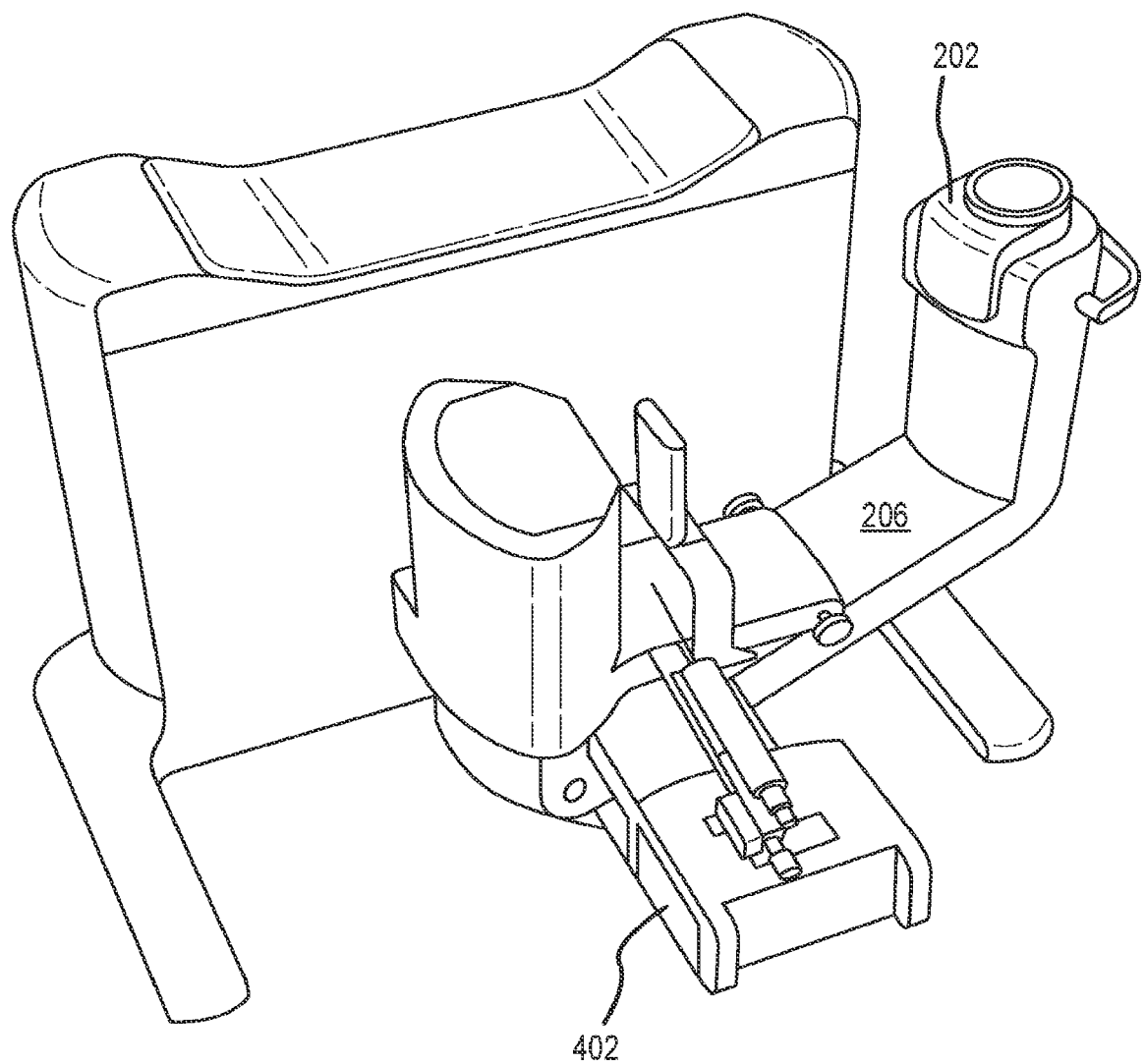
Figure 6:
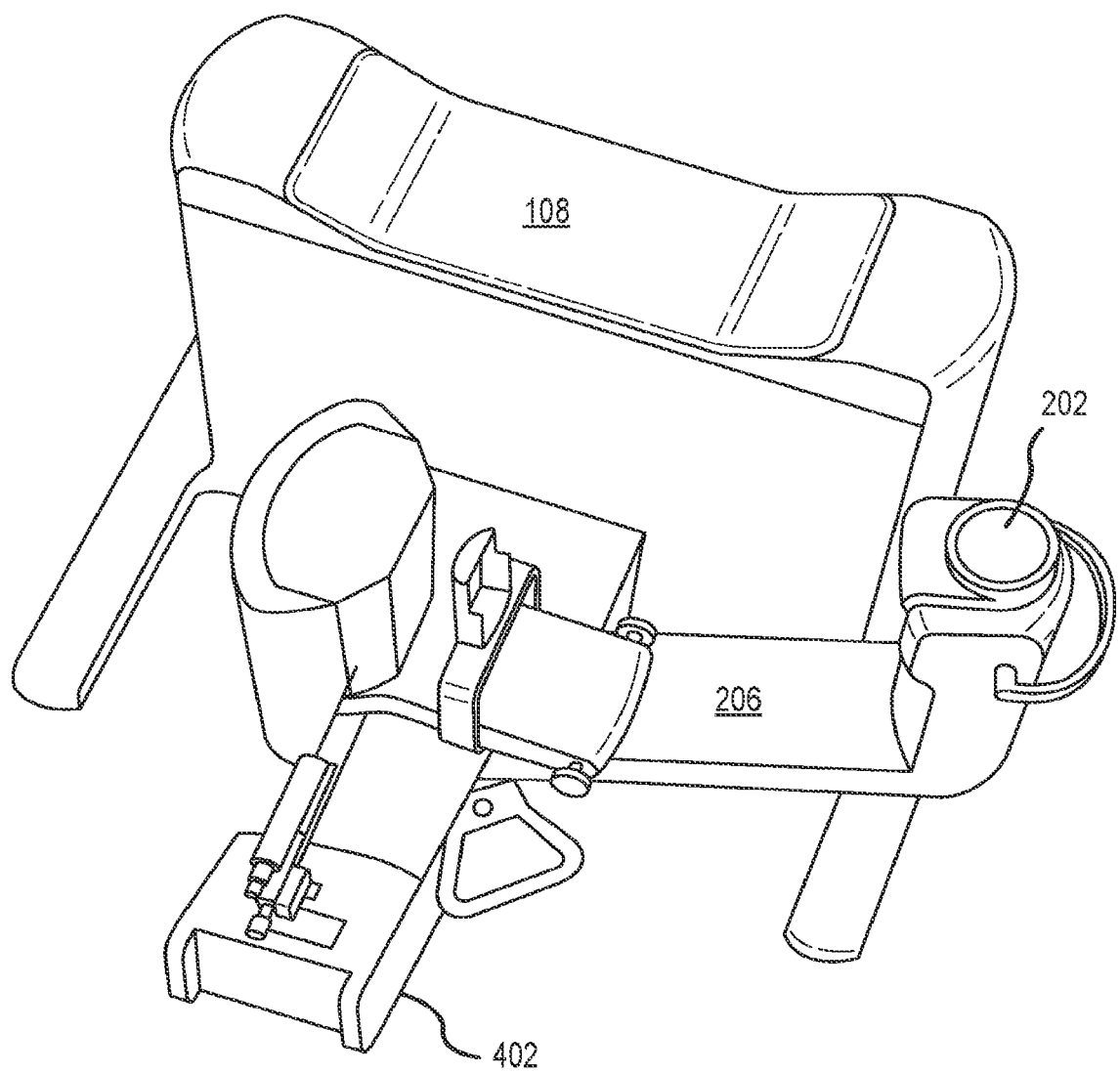
Figure 7:
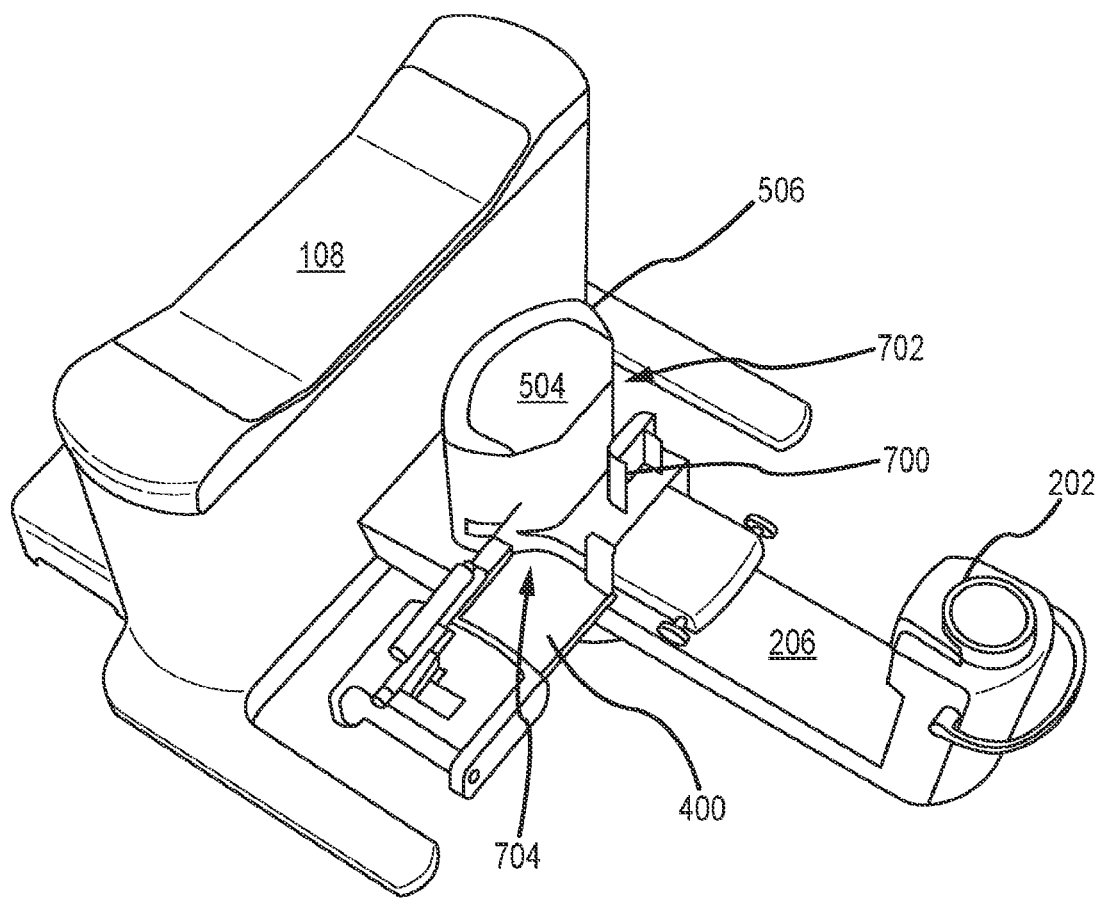

Referring to FIG. 1, a biopsy station 100 for performing tomotactic guided breast biopsy in prone may include a tomosynthesis imaging system 102 and a stage arm assembly 104 positioned below a biopsy table 106. The tomosynthesis imaging system and stage arm assembly are used for needle guidance. As explained in greater detail below, either or both the imaging system and stage arm assembly may be repositionable in one or more dimensions to facilitate the biopsy procedure. An example of a tomosynthesis imaging system is described in U.S. Pat. No. 7,869,563, which is hereby incorporated by reference, and sold commercially as Selenia® Dimensions® digital breast tomosynthesis system from Hologic, Inc. It should be noted, however, that the biopsy station is not limited to use with tomosynthesis imaging, and could utilize one or more of tomotactic, stereotactic, and other forms of guidance.

The biopsy table 106 is supported by a footed base 108. The base is offset to one side of the table such that an area beneath the table is available for positioning both a portion of the body of the patient on which the biopsy is performed and equipment for performing the biopsy. The table 106 includes a rigid platform which, may be cantilevered from the base 108, and which supports the patient during the biopsy procedure. The platform may be partially or wholly covered with padding for the comfort of the patient. The table may be contoured such that symmetrical distal end sections 110, 112 are elevated relative to a central section 114. Either of the elevated sections 110, 112 can help support the legs of the patient, thereby allowing 180 degree repositioning of the patient. The central section 114 supports the head, abdomen and hip of the patient. Transitions between the end sections and the central section are angled to provide comfortable head, abdomen and hip support. An aperture 116 in the central section 114 of the table enables a portion of the body of the patient to extend below the table when the patient is situated in a prone position. For example, the breast being biopsied may extend through the aperture. Other parts of the patient's body may also extend through the aperture, e.g., an arm, for enhanced comfort or positioning for the biopsy procedure. Some aspects of the table may be consistent with features described in International Application Number PCT/US11/61186, titled TABLE FOR PERFORMING MEDICAL PROCEDURES, filed Nov. 17, 2011, and U.S. Pat. No. 5,289,520, titled STEREOTACTIC MAMMOGRAPHY IMAGING SYSTEM WITH PRONE POSITION EXAMINATION TABLE AND CCD CAMERA, filed Oct. 6, 1992, both of which are incorporated by reference.

Referring now to FIGS. 1-7, an equipment support platform 200 is cantilevered from the base 108 beneath the table in the Y-dimension. The equipment support platform may be statically or repositionably connected to the base, and may move in a coordinated manner with, or independent of, the table based on settings which can be changed by an operator. The support platform may be connected to the base via a Y-axis slide assembly which enables the support platform to move relative to the base in the Y-dimension. An X-axis slide assembly may enable the support platform to move relative to the base in the X-dimension. Range of motion may be approximately +/−4 inches relative to a Z-axis defined by the center of the aperture. A handle connected to the support platform facilitates manual positioning of the platform by an operator. Slide lock features may be employed to secure the platform in a desired position.

The tomosynthesis imaging system 102 is mounted on the equipment support platform 200. The imaging system may include an x-ray energy source 202 and an x-ray energy receptor 204 (shown via cutaways in FIGS. 2 and 4). The source and receptor are aligned such that the receptor detects energy emitted by the source. The energy source 202 is positioned on a first upright portion of a support arm 206 such as a c-arm, and the energy receptor 204 is positioned on a second upright portion of the support arm. The support arm 206 helps maintain the receptor 204 and energy source 202 in alignment at a fixed distance, thereby mitigating or eliminating the need for focus adjustment. The support arm 206 is connected to the support platform 200 via a pivoting connector such as a bearing. As will be explained in greater detail below, during a scan or sweep the support arm moves under motor control such that the energy source 202 moves along an arc 300 (see FIG. 4 specifically) defined by a Z-axis of rotation 302 defined by a pivoting connector such as a bearing. The receptor 204 moves along an arc 301 characterized by a smaller radius than arc 300 because the pivoting connector via which the support arm is connected to the support platform is nearer to the second upright portion of the c-arm than the first upright portion of the c-arm. A handle 308 connected to the first upright portion facilitates manual rotational positioning of the support arm 206 within a 180 degree range of motion in the X-Y plane during set up by an operator. Consequently, a path 306 of x-ray energy defined between the energy source 202 and receptor 204 in the X-Y plane can be reoriented within the X-Y plane with respect to the patient's breast through the 180 degree range of motion during set up. Moreover, because the position of the patient can be reversed (changed 180 degrees horizontally in the X-Y plane), the biopsy needle is effectively positionable through 360 degrees in the X-Y plane relative to the breast.

The biopsy gun stage arm assembly 104 is connected to the support platform 200 via a pivoting connector such as a bearing. Moreover, the stage arm assembly may pivot around a Z-axis which is coincident with Z-axis 302, and a multi-part bearing assembly may be utilized to enable independent rotational movement of the imaging system and the stage arm assembly. Optionally, the stage arm assembly may rotate about an axis offset from that of the imaging system. A rotatable support platform 400 associated with the stage arm assembly is disposed above the support arm 206. The stage arm assembly is rotatable through 180 degrees in the X-Y plane for manual set up by the operator. The stage arm assembly may be secured against rotational movement by a brake mechanism, e.g., to inhibit motion during a sweep or scan. A guidance module 402 with an interface and display mounted in a housing integral with or connected to the support platform displays tomosynthesis images and information about the relative locations of the targeted feature and the biopsy gun 404 to help position the biopsy gun and guide its path of travel such that the needle intersects with the target feature. A stage arm 406 is disposed on top of the guidance module 402 housing. A carriage slide assembly 408 is connected to the stage arm. A gun mount is connected to the carriage slide assembly. A biopsy gun 404 is mounted to the gun mount. The stage arm assembly may be oriented such that the operational path of travel of the biopsy gun needle intersects the Z-axis 302 about which the stage arm assembly and support arm rotate. More particularly, the orientation of the stage arm assembly may be such that the operational path of travel of the biopsy gun needle intersects the Z-axis about which the stage arm assembly and support arm rotate at a particular point within the field of view of the tomosynthesis imaging system. The carriage slide assembly enables manual or motor-driven adjustment of the distance between the needle and the rotational Z-axis intersection point. The stage arm (and thus the gun mount and biopsy needle) may be oriented at a fixed inclination, e.g., 10°, relative to the X-Y plane in which the stage arm assembly is rotatable. Inclination of the stage arm allows a "zero degree" offset configuration in which the stage arm assembly is aligned with the imaging system as specifically shown in FIG. 2. Optionally, the stage arm assembly is offset from that of the imaging system, e.g., the stage arm assembly is not aligned with the imaging system. In particular, the inclined biopsy gun and needle do not reside in the field of view of the imaging system so the images are free of biopsy needle artifacts. Offset configurations in which the stage arm assembly is approximately orthogonal to the imaging system are specifically shown in FIGS. 3-7. Some aspects of the stage arm assembly may be consistent with U.S. patent application Ser. No. 12/715,591, titled NEEDLE BREAST BIOPSY SYSTEM AND METHOD FOR USE, filed Mar. 2, 2010, which is incorporated by reference.

A breast support assembly is provided to place the breast in compression. The breast support assembly includes a breast support platform 504 and compression paddle 502 connected to a rotatable platform 500. The platform 500 of the breast support assembly is connected to the support platform 200 via a pivoting connector such as a bearing. Moreover, the stage arm assembly may pivot around a Z-axis which is coincident with Z-axis 302, and a multi-part bearing assembly may be utilized to enable independent rotational movement of the breast support assembly. Optionally, the stage arm assembly pivots about an axis that is offset from Z-axis 302. The compression paddle is linearly movable toward and away from platform 504 in order to compress the breast against the foremost surface of the breast support platform 504 and release the breast from compression upon completion of the procedure. An aperture in the compression paddle allows a biopsy needle to traverse the compression paddle, e.g., in the zero degrees offset configuration. The breast support platform 504 may be integral to a protective cover 506 which encloses the receptor 204. A gap, e.g., 3 cm, between the foremost surface 700 (see FIG. 7) of the breast support platform and the receptor 204 allows the receptor to move during a scan or sweep without interfering with the stationary protective cover and breast support platform. Movement of the receptor during a scan or sweep and the gap enable use of a reduced size receptor. Use of the reduced size receptor enables use of a reduced size foremost surface 700. The breast support platform and/or protective cover may have side-edge sections 702, 704 adjacent to the foremost surface 700 which are angled, curved or otherwise formed away from surface 700 in order provide free space where the protective cover or breast support platform might otherwise interfere with the biopsy gun. For example, and without limitation, use of a 15 cm width receptor and a corresponding size foremost surface allows a side-edge section geometry which facilitates biopsy of relatively thin breasts in the ninety degree offset configuration by avoiding interference between the breast support platform and/or protective cover and the biopsy gun and stage arm assembly. Moreover, the present invention also facilitates access to previously inaccessible lesions, for example, such as those that may be situated in the axilla which prior conventional detectors would be unable to access.

The stage arm assembly 104 and imaging system 102 are independently rotatable for set up, e.g., each through a 180 degree range of arc in the X-Y plane. More particularly, the furthest extent to which the stage arm assembly protrudes from the Z-axis of rotation is less than the minimum distance between the first upright portion of the support arm and the Z-axis of rotation. Consequently, the stage arm assembly can be rotated to either side of the receptor without interference. Similarly, the stage arm assembly can be rotated to either side of the breast support assembly without interference. (compare, e.g., FIG. 3 with FIG. 7) As specifically illustrated in FIG. 2, the stage arm assembly and breast support assembly may also be optionally aligned.

Figure 8:
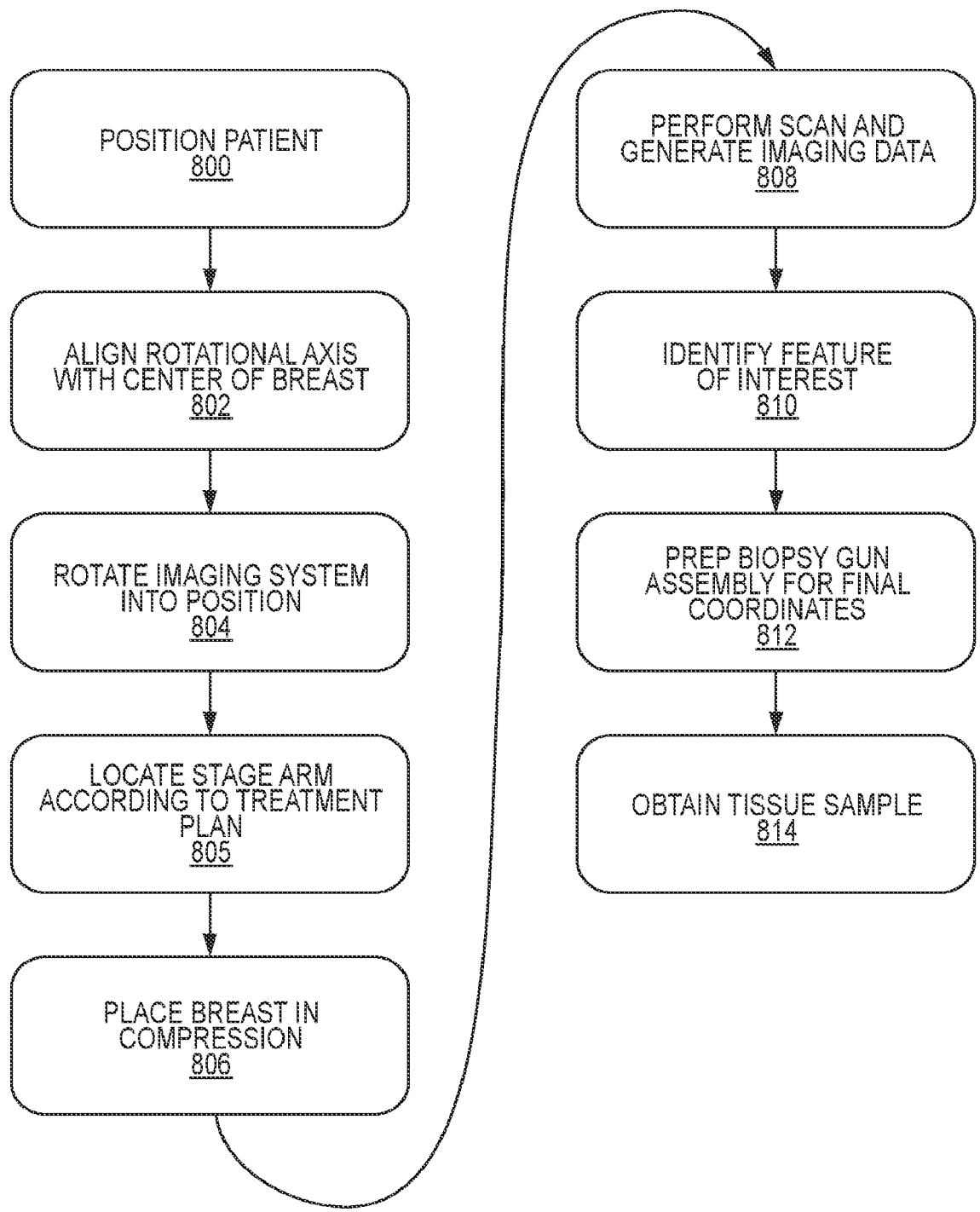
FIG. 8 is a flow diagram of a biopsy procedure.

Some or all of the features described above may be used to facilitate a breast biopsy procedure illustrated in FIG. 8. In order to perform a biopsy procedure the patient is positioned on the table with one or both breasts and possibly one arm protruding through the aperture in step 800. As previously noted, the patient can be oriented in at least two different positions which are offset horizontally by 180 degrees in the X-Y plane. The breast which is the subject of the biopsy procedure may be approximately centered in the Z-axis about which the stage arm assembly and support arm rotate. The equipment support platform may then be moved in one or more dimensions orthogonal to the Z-axis to help center the breast in the axis of rotation in step 802. The imaging system orientation is then adjusted until a desired orientation is obtained for the procedure to be performed, as indicated in step 804. For example, the imaging system may be moved rotationally about the Z-axis, and raised or lowered along the Z-axis. The stage arm assembly orientation is then adjusted for the procedure to be performed, as indicated in step 805. For example, the stage arm assembly may be moved rotationally about the Z-axis and the location of the gun mount on the carriage slide assembly may be adjusted. The patient's breast is then immobilized between a compression paddle and the receptor in step 806. A tomosynthesis scan is performed by moving the x-ray energy source along an arc centered on the top surface of the receptor at step 808. The axis of rotation of the x-ray energy source can optionally be located about 3 cm above the compressed breast, the breast platform, or the top surface of the breast platform. Such an axis of rotation may reduce the amount of blurring in a sweep or movement of the x-ray energy source during a tomosynthesis scan. As an example, at predetermined discrete positions the energy source may be energized to emit a collimated x-ray beam, e.g., at every 1.07° of an arc of +/−7.5°. The motion of the energy source can be continuous or discontinuous. If motion is continuous, a respective set of image data is accumulated over a small increment of continuous motion, e.g., a 0.1° to 0.5° arc of motion of source, although these non-limiting parameters are only an example. Different ranges of motion of the energy source can be used, and the motion of the source may be along an arc centered at a different axis, such as inside the immobilized breast, at the receptor, or elsewhere. During the scan, the x-ray beam irradiates the breast, and radiation that has passed through the breast is received by the receptor. The receptor and associated electronics generate image data in digital form for each pixel of a rectangular grid of pixels at each predetermined discrete angular position of source. An associated three-dimensional image is generated and presented on the display. The image data is used to identify the precise location (final coordinates) of the previously detected feature of interest in step 810. Various fine-adjustment settings may be calculated and used to complete preparation of the stage arm assembly and biopsy gun in step 812. The needle is then actuated in order to obtain a tissue sample in step 814. Any biopsy system may work with the present invention. For example, tubing couples the biopsy needle with a vacuum console and filter for capturing excised tissue samples. The stage arm assembly and other parts of the station may be reconfigured to obtain as many samples as required.

While the invention has been described through the above examples and features, it will be understood by those of ordinary skill in the art that a wide variety of modifications, combinations and variations of the examples and features may be made without departing from the inventive concepts herein disclosed. Moreover, the invention should not be viewed as being limited to any specific purposes described herein, but rather should be viewed as being applicable to accomplish a wide variety of purposes beyond those described herein.

The invention claimed is:

1. An apparatus comprising:
   a base;
   an equipment support platform linearly positionable relative to the base;
   a tomosynthesis imaging system rotatably secured to the equipment support platform for imaging a breast of a patient, wherein the tomosynthesis imaging system is rotatable about an imaging system rotation axis, wherein the tomosynthesis imaging system comprises an x-ray source and a receptor;
   a stage arm assembly rotatably secured to the equipment support platform, wherein the stage arm assembly comprises a biopsy needle configured to obtain a tissue sample from the breast of the patient, wherein the stage arm assembly is rotatable about a stage arm assembly rotation axis; and
   a breast support assembly linearly positionable along the equipment support platform, wherein the breast support assembly is configured to immobilize the breast of the patient during an image-guided biopsy procedure, wherein the breast support assembly comprises a breast support platform and a compression paddle, the breast support platform integral with a protective cover enclosing the receptor.

2. The apparatus of claim 1, wherein the equipment support platform is positionable along a Z-axis, the Z-axis being oriented in a same direction as at least one of the imaging system rotation axis and the stage arm assembly rotation axis.

3. The apparatus of claim 2, further comprising a table positioned above the equipment support platform, wherein the table is configured to support the patient in a prone position.

4. The apparatus of claim 3, wherein the table defines an aperture through which the breast imaged by the tomosynthesis imaging system extends.

5. The apparatus of claim 4, wherein the Z-axis is defined by the aperture.

6. The apparatus of claim 2, wherein the equipment support platform is configured to be moved in one or more dimensions orthogonal to the Z-axis.

7. The apparatus of claim 2, wherein the tomosynthesis imaging system is positionable along the Z-axis.

8. The apparatus of claim 2, wherein the stage arm assembly is positionable along the Z-axis.

9. The apparatus of claim 1, wherein the imaging system rotation axis is defined between the x-ray source and the receptor.

10. The apparatus of claim 9, wherein a portion of the biopsy needle is configured to be positioned within a path of x-ray emission from the x-ray source.

11. The apparatus of claim 1, wherein the stage arm assembly is configured to be rotated to either side of the breast support assembly without interfering with the breast support assembly.

12. The apparatus of claim 1, wherein the stage arm assembly is independently rotatable from the tomosynthesis imaging system.

13. The apparatus of claim 1, wherein the stage arm assembly is independently linearly positionable from the tomosynthesis imaging system.

14. The apparatus of claim 1, wherein the imaging system rotation axis is co-axial with the stage arm assembly rotation axis.

15. The apparatus of claim 1, wherein the stage arm assembly is rotatable through at least 180 degrees.

16. The apparatus of claim 1, wherein the biopsy needle is positionable through 360 degrees relative to the breast.

17. The apparatus of claim 1, wherein the compression paddle is linearly movable toward and away from the breast support platform.

18. The apparatus of claim 1, further comprising a carriage slide assembly connected to the stage arm assembly, wherein the carriage slide assembly is configured to reposition the biopsy needle.

19. The apparatus of claim 1, wherein the breast support platform or the protective cover have side-edge sections configured to provide access to the immobilized breast of the patient.

20. A method of performing an image-guided biopsy procedure, the method comprising:
   extending a breast of a patient through an opening of a patient support table when the patient is in a prone position;
   compressing the breast of the patient with a breast support assembly, wherein the breast support assembly is linearly positionable relative to an equipment support platform disposed below the table, wherein the breast support assembly includes a breast support platform and a compression paddle that the breast of the patient is compressed between;

rotatably positioning a tomosynthesis imaging system about an imaging system rotation axis, wherein the tomosynthesis imaging system is rotatably secured to the equipment support platform for imaging the breast of the patient, wherein the tomosynthesis imaging system is positionable independent of the breast support assembly, wherein the tomosynthesis imaging system includes an x-ray source and a receptor, the receptor enclosed within the breast support platform that is integral with a protective cover; and rotatably positioning a stage arm assembly relative to the breast support assembly, wherein the stage arm assembly is positionable independent of the breast support assembly, and wherein the stage arm assembly comprises a biopsy needle configured to obtain a tissue sample from the breast of the patient, wherein the stage arm assembly is rotatable about a stage arm assembly rotation axis and positionable along a Z-axis, the Z-axis being oriented in a same direction as at least one of the imaging system rotation axis and the stage arm assembly rotation axis.

* * * * *